United States Patent [19]
Tuckey et al.

[11] Patent Number: 5,951,569
[45] Date of Patent: Sep. 14, 1999

[54] STENT DELIVERY SYSTEM

[75] Inventors: Joel F. Tuckey, Encinitas; Garry Eugene Rupp, Santee, both of Calif.

[73] Assignee: Medtronic, Inc., Minneapolis, Mass.

[21] Appl. No.: 09/085,776

[22] Filed: May 28, 1998

Related U.S. Application Data

[62] Division of application No. 08/841,213, Apr. 29, 1997, Pat. No. 5,810,871.

[51] Int. Cl.$^6$ ........................................ A61F 11/00
[52] U.S. Cl. ............................................ 606/108; 128/898
[58] Field of Search .................... 606/108, 191, 606/194, 195, 198; 128/898

[56] References Cited

U.S. PATENT DOCUMENTS

| | | | |
|---|---|---|---|
| 4,886,062 | 12/1989 | Wiktor | 128/343 |
| 4,950,227 | 8/1990 | Savin et al. | 604/8 |
| 5,108,416 | 4/1992 | Ryan et al. | 606/194 |
| 5,192,297 | 3/1993 | Hull | 606/195 |
| 5,192,307 | 3/1993 | Wall | 623/1 |
| 5,266,073 | 11/1993 | Wall | 623/1 |
| 5,360,401 | 11/1994 | Turnland | 604/96 |
| 5,409,495 | 4/1995 | Osborn | 606/108 |
| 5,439,445 | 8/1995 | Kontos | 604/96 |
| 5,443,495 | 8/1995 | Buscemi et al. | 623/1 |
| 5,445,646 | 8/1995 | Euteneur et al. | 606/198 |
| 5,453,090 | 9/1995 | Martinez et al. | 604/53 |
| 5,507,768 | 4/1996 | Lau et al. | 606/198 |
| 5,522,882 | 6/1996 | Gaterud et al. | 623/1 |
| 5,545,209 | 8/1996 | Roberts et al. | 623/1 |
| 5,562,620 | 10/1996 | Klein et al. | 604/96 |
| 5,569,295 | 10/1996 | Lam | 606/198 |
| 5,639,274 | 6/1997 | Fischell et al. | 606/96 |
| 5,846,246 | 12/1998 | Dirks et al. | 606/108 |

FOREIGN PATENT DOCUMENTS

| | | |
|---|---|---|
| 0 408 245 A1 | 1/1991 | European Pat. Off. . |
| 0 442 657 A2 | 8/1991 | European Pat. Off. . |
| 0 696 447 A2 | 2/1996 | European Pat. Off. . |
| WO 96/31174 | 10/1996 | WIPO . |
| WO 96/31249 | 10/1996 | WIPO . |
| WO 96/33677 | 10/1996 | WIPO . |
| WO 97/07756 | 3/1997 | WIPO . |
| PCT/US 98/05957 | 3/1998 | WIPO . |

*Primary Examiner*—Michael Buiz
*Assistant Examiner*—Kevin Troung
*Attorney, Agent, or Firm*—Dianne Plunkett Latham; Harold R. Patton

[57] ABSTRACT

What is disclosed is a stent delivery system comprising an inflation shaft having an expandable balloon sealingly mounted at the distal end thereof and a tubular sheath having the inflation shaft longitudinally running therethrough. The tubular sheath has an expandable sheath at the distal end thereof with the balloon longitudinally running therethrough and an expandable stent mounted on the expandable sheath. Also disclosed is a method of delivering a stent into a body lumen. The method comprises the steps of providing an inflation shaft having an expandable balloon sealingly mounted at the distal end thereof and providing a tubular sheath having the inflation shaft longitudinally running therethrough. The expandable sheath has the balloon longitudinally and slidingly running therethrough, and an expandable stent is mounted on the expandable sheath. The stent is positioned in the body lumen at the treatment site and the balloon is inflated simultaneously with the expandable sheath to deploy the stent.

7 Claims, 4 Drawing Sheets

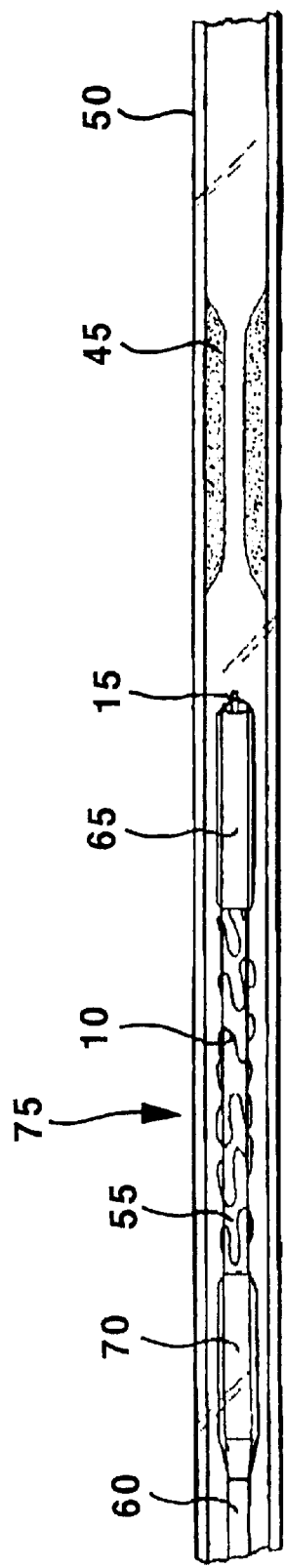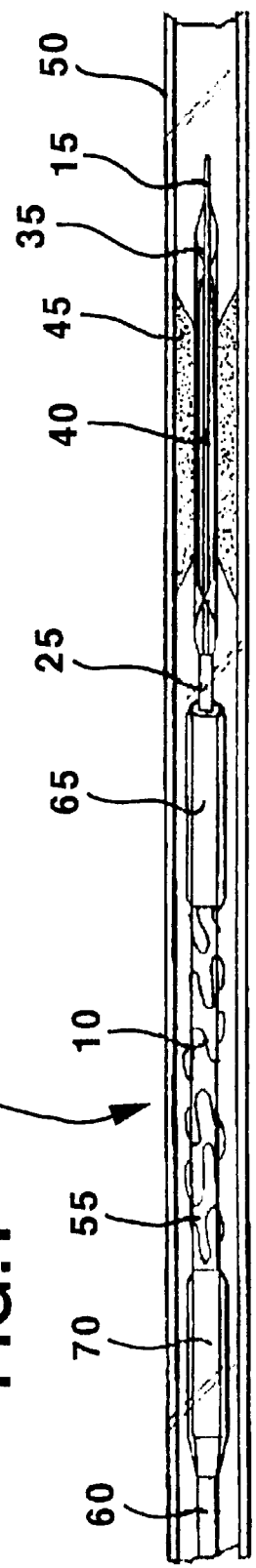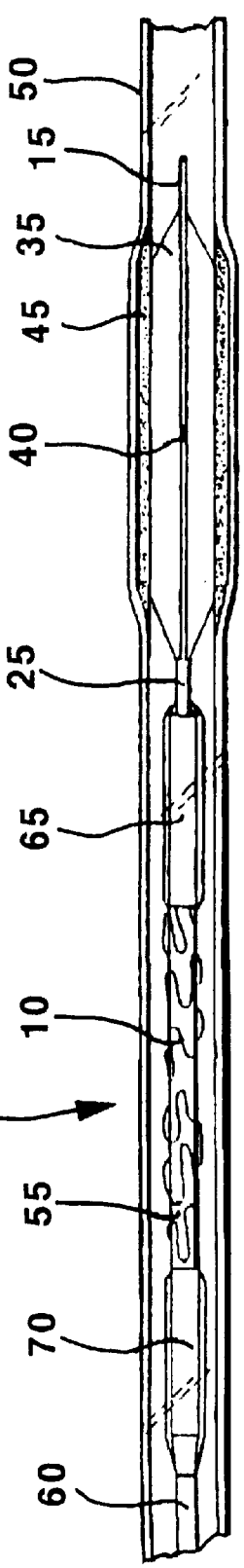

STENT DELIVERY SYSTEM

This application is a divisional of application Ser. No. 08/841,213 filed Apr. 29, 1997 now U.S. Pat. No. 5,810,871.

FIELD OF THE INVENTION

The present invention relates to intravascular stent implants for maintaining vascular patency in humans and animals and more particularly to a stent delivery system in the form of a sheath having a stent positioned thereon with anchoring end caps at either end of the stent.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to stent delivery systems for acute and chronic closure or reclosure of any body lumen.

A typical stent is a cylindrically shaped wire formed device intended to act as a permanent prosthesis. A typical stent ranges from 5 mm to 50 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the interior of the body lumen thereby forming a supporting relationship with the vessel walls.

The biocompatible metal stent props open blocked coronary arteries, keeping them from reclosing after balloon angioplasty. In a typical prior art procedure a balloon of appropriate size and pressure is first used to open the lesion. The process is repeated with a stent crimped on a second balloon. The second balloon may be of higher pressure, e.g., more than 12 atmospheres, to insure that the stent is fully deployed upon inflation. The stent is deployed when the second balloon is inflated. The stent remains as a permanent scaffold after the balloon is withdrawn. The stent must be forced against the artery's interior wall so that it will fully expand thereby precluding the ends of the stent from hanging down into the channel encouraging the formation of thrombus.

Various shapes of stents are known in the art. U.S. Pat. No. 4,886,062 to Wiktor for "Intravascular Radially Expandable Stent and Method of Implant" discloses a two-dimensional zig-zag form, typically a sinusoidal form.

End caps to anchor the proximal and distal ends of stents are seen in U.S. Pat. No. 4,950,227 to Savin et al. for "Stent Delivery System, U.S. Pat. No. 5,108,416 to Ryan et al. for "Stent Introducer System", U.S. Pat. No. 5,443,495 to Buscemi et al. for "Polymerization Angioplasty Balloon Implant Device" and WO 96/31249 to Solar for "Non-Deformable Self-Expanding Parallel Flow Endovascular Stent and Deployment Apparatus Therefor".

Stent delivery systems using sheaths over the stents can be seen in U.S. Pat. No. 5,192,297 to Hull, U.S. Pat. No. 5,360,401 to Turnland et al. or U.S. Pat. No. 5,453,090 to Martinez et al.

U.S. Pat. Nos. 5,192,307 and 5,266,073 to Wall discloses coaxial catheters with the outer catheter being manipulated to urge the stent in place over the balloon. After the stent is over the balloon, the balloon will be inflated to urge the stent outwardly to its opened condition.

Stent delivery systems wherein the sheath is on the exterior of the stent are disadvantageous because such systems require the use of multiple balloon catheters which is costly and requires more operator time. Stent delivery systems with exposed stents without end caps are disadvantageous because the proximal or distal end of the stent may snag during delivery or retraction.

SUMMARY OF THE INVENTION

It is an object of the invention to provide a stent delivery system which reduces the possibility of snagging the proximal or distal end of the stent during delivery or retraction and which permits the balloon to be advanced and retracted independently of the stent prior to stent deployment. It is a further object of the invention to reduce the need for multiple devices such as balloon catheters during dilation and stent delivery.

The present invention is accomplished by providing a method and apparatus for a radially expandable stent delivery system for implantation within a body vessel. What is disclosed is a stent delivery system comprising an inflation shaft having an expandable balloon sealingly mounted at the distal end thereof and a tubular sheath having the inflation shaft longitudinally running therethrough. The tubular sheath has an expandable sheath at the distal end thereof with the balloon longitudinally running therethrough and an expandable stent mounted on the expandable sheath.

Also disclosed is a method of delivering a stent into a body lumen. The method comprises the steps of providing an inflation shaft having an expandable balloon sealingly mounted at the distal end thereof and providing a tubular sheath having the inflation shaft longitudinally running therethrough. The expandable sheath has the balloon longitudinally and slidingly running therethrough, and an expandable stent is mounted on the expandable sheath. The stent is positioned in the body lumen at the treatment site and the balloon is inflated simultaneously with the expandable sheath to deploy the stent.

BRIEF DESCRIPTION OF THE DRAWINGS

FIG. 1 is a plan view of a stent delivery system positioned proximal to the lesion;

FIG. 2 is a plan view of a PTCA balloon extended out of the sheath and crossing the lesion;

FIG. 3 is a plan view of an inflated balloon dilating the lesion;

DETAILED DESCRIPTION OF THE PREFERRED EMBODIMENTS

Figure 4:
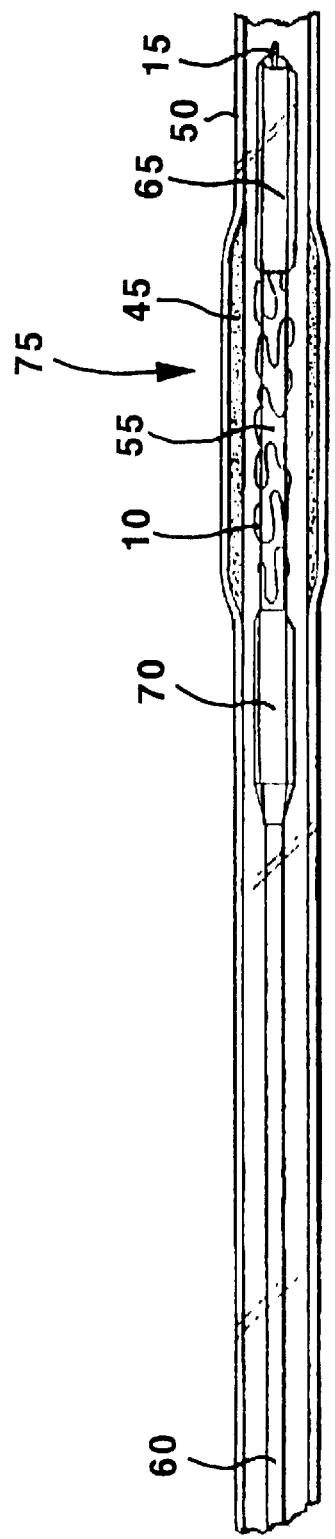
FIG. 4 is a plan view of a deflated balloon retracted back into the sheath and the delivery system positioning the stent in the target lesion.

A typical stent may be formed with a wire segment which is formed into a sinusoidal wave form helix pattern the length of the stent 10 by a means such as passing the wire through gears such as those disclosed in U.S. Pat. No. 2,153,936 issued to Owens et al. and formed into a stent using methods disclosed in U.S. Pat. No. 4,886,062 to Wiktor. Those skilled in the art would recognize that other means of stent formation may also be used. Although coronary applications are described herein, applicant's stent delivery system 75 could be used for any type of stent including peripheral or neurological, for example. Although a stent with a helical pattern is described herein, those skilled in the art would recognize that other stent shapes could be used as well, including a tubular stent.

The stent 10 is placed over a suitable expandable diameter device such as an inflatable balloon 35 which is typically used for angioplasty procedures. A stent can be implanted during a single angioplasty procedure by using a balloon catheter bearing a stent 10 which has been crimped by hand or with a suitable crimping tool (not shown) onto the balloon. Applying a stent directly to a balloon 35 can result in damage to the balloon such as punctures. Placing a expandable elastomeric sheath 55 between the balloon 35 and stent 10 reduces the possibility of damage to the balloon. The sheath 55 expands with the balloon 35 during stent 10 deployment. Applying the stent 10 directly to the balloon 35 also precludes the balloon from being advanced independently of the stent prior to stent deployment. Applying the stent to a expandable sheath 55 which is over the balloon permits the balloon to be advanced without the stent prior to deployment so that the lesion 45 within a vessel 50 can be predialated prior to stent 10 deployment. The optional predialation can occur as many times as needed prior to stent 10 deployment. Such a stent delivery system 75 reduces the need and cost of multiple devices as well as reducing the time spent during the procedure because it eliminates the need to swap out devices. The expandable sheath 55 can be made of a material such as an elastic polymer with a wall thickness of between 0.002 inches and 0.010 inches. The expandable sheath 55 should be long enough to cover the area under the stent 10 and extend 3 mm beyond the stent 10 proximal end and 3 mm beyond the stent 10 distal end. The expandable sheath 55 could range from 2 mm to 10 mm in length.

A physician may need to remove a stent delivery system 75 with the stent 10 still intact on the balloon 35. In such circumstances the wound wire stent coils or the tubular ends of tubular stents and grafts may snag on the guide catheter upon entering the guide catheter. A distal end cap 65 releasably covers at least the last row of stent 10 loops and a proximal end cap 70 releasably covers at least the first row of stent loops 10 may eliminate this problem. The proximal end cap 70 is about two and one-half centimeters long with a length ranging between 2 mm and 30 mm. The distal end cap 65 is about one-half centimeter long with a length ranging between 2 mm and 30 mm. The end caps 65, 70 can be made of any suitable polymer such as polyethylene (PE) or Nylon which is compatible with the bonding surface. The single wall thickness of end caps 65, 70 ranges between 0.0005 inches and 0.005 inches. The proximal end of the proximal end cap 70 is affixed to the stiffer sheath section 60 as for example with adhesive 80. The distal end of the distal end cap 65 is affixed to the distal end of the expandable sheath section 55 as for example with adhesive 80. As the balloon 35 is expanded, the angle of the proximal cone 85 or distal cone 90 causes the end caps 65, 70 to slide back off the stent 10 coils. The end caps 65, 70 can be scored to induce a split and aid in the retraction.

Adhesives 80 may be made from Cyanoacrylates such as Loctite® manufactured by Loctite Corp. in Hartford Conn., or from ultraviolet light cured adhesives, or from polyurethane adhesives available from the H. B. Fuller Co. of St. Paul, Minn. A radio frequency bond could also be substituted for adhesive 80.

Figure 5:
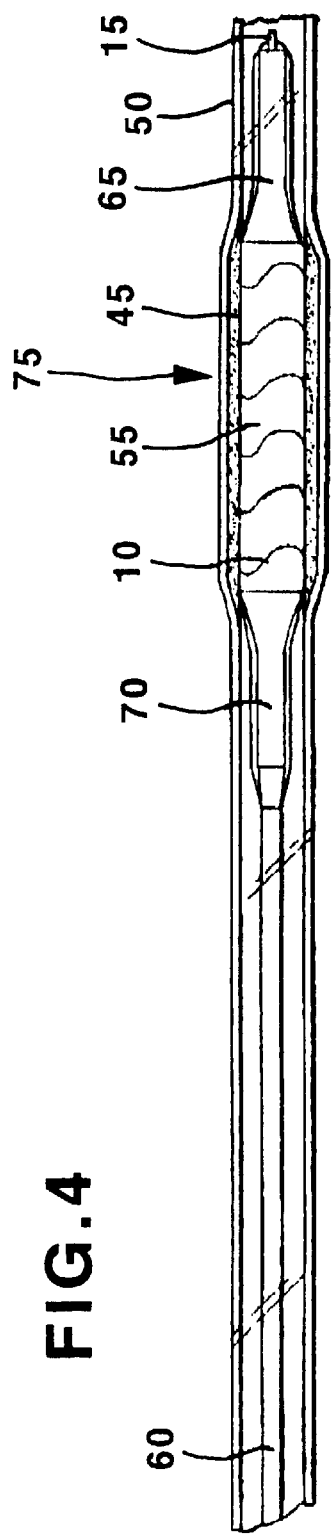
FIG. 5 is a plan view a reinflated balloon deploying the stent by inflating the portion of the sheath that is under the stent.
Figure 6:
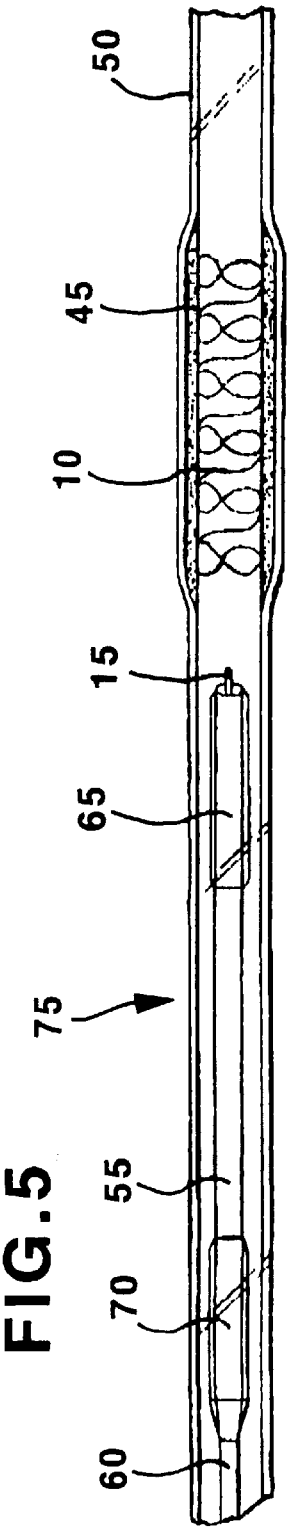
FIG. 6 is a plan view of the deflated balloon retracted into the sheath and the delivery system withdrawn from the stent.
Figure 7:
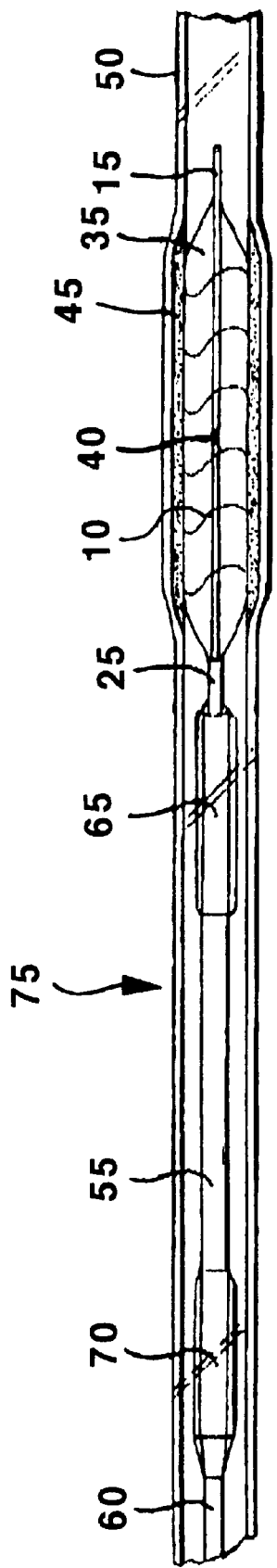
FIG. 7 is a plan view of a reinflated balloon in a post dilation procedure.

For the stent delivery system 75 deployment procedure refer to FIGS. 1 through 7. FIG. 1 shows the stent delivery system 75 positioned proximal to the lesion 45. FIG. 2 shows the balloon 35 emanating from the stent delivery system 75 and advanced into the lesion 45. Once the balloon 35 is lodged in the lesion 45, the balloon 35 can be inflated as seen in FIG. 3 using standard angioplasty procedures and techniques to dilate the lesion 45. In FIG. 4 the balloon 35 is deflated and retracted back into the stent delivery system 75. The stent delivery system 75 is then advanced across the lesion 45 so that the stent 10 covers the target lesion 45. In FIG. 5 the balloon 35 is reinflated to deploy the stent 10. The balloon 35 thereby inflates the portion of the expandable sheath 55 which is under the stent 10. The stent 10 is thereby radially expanded as the balloon 35 is inflated, causing the stent 10 to contact the body lumen thereby forming a supporting relationship with the vessel walls as seen in FIG. 5. As the balloon 35 expands, so does the stent 10. The expanding balloon 35 together with the stent 10 further compress the lesion 45 and prevents possible reocclusion. When the angioplasty procedure is completed, balloon 35 is deflated and withdrawn leaving stent 10 firmly implanted within vessel 50 as seen in FIG. 6. The previously occluded vessel 50 is recannalized and patency is restored. After stent 10 delivery it may be desirable to post dilate the lesion 45 as shown in FIG. 7. This can occur as many times as necessary by positioning the balloon 35 in the lesion 45 and reinflating the balloon.

Figure 8:
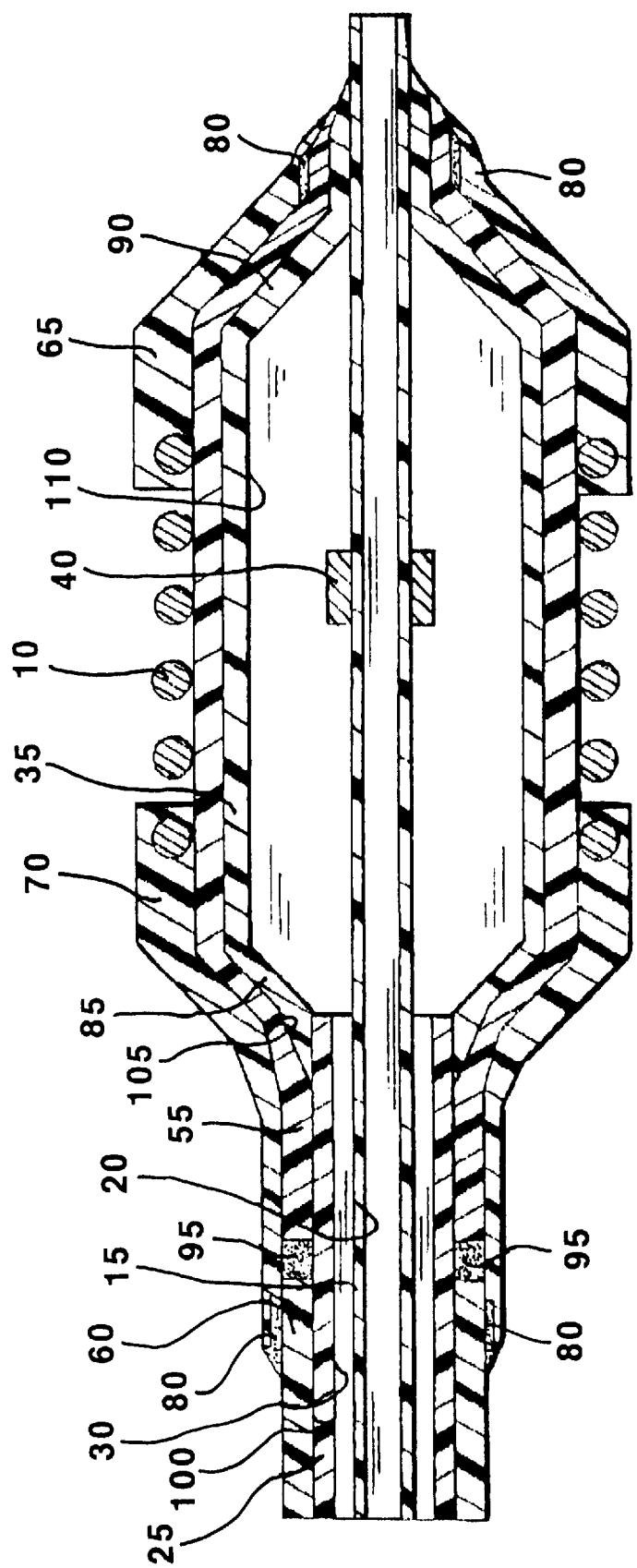
FIG. 8 is a longitudinal cross section of a stent mounted on an expanding balloon within a sheath just before the end caps are released from the stent ends.

A longitudinal cross-section of an inflating balloon in applicant's stent delivery system 75 is shown in FIG. 8. The stent 10 is centrally located and positioned with respect to the length of balloon 35. The stent 10 turns are evenly spaced so that when the stent 10 begins to expand as shown in FIG. 8, the stent 10 will provide even support inside vessel 50, and resist external loading. The balloon catheter shown in FIG. 8 is a conventional over-the-wire catheter having a guidewire shaft 15 with one or more radiopaque marker bands 40 mounted between the proximal and distal ends of the balloon 35. An inflation shaft 25 provides fluid communication with the balloon 35. The balloon has a proximal cone 85 and a distal cone 90. It is understood that any type of catheter balloon could be used, as for example, a rapid exchange catheter or a perfusion catheter.

The proximal end of balloon 35 is bonded to the distal end of the inflation shaft 25 by any conventional means such as heat bonding or adhesives. Adhesives may be made from Cyanoacrylates such as Loctite® manufactured by Loctite Corp. in Hartford Conn., or from ultraviolet light cured adhesives, or from polyurethane adhesives available from the H. B. Fuller Co. of St. Paul, Minn. A radio frequency bond could also be substituted for adhesive. The balloon 35 is advanced distally from or retracted proximally into the expandable sheath 55 by a means such as advancing the inflation shaft 25 to which the balloon 35 is affixed.

To enhance pushability, the proximal end of the expandable sheath section 55 is attached to a stiffer sheath section 60 which can be made of polyethylene (PE), Nylon, polyimide or PEBAX. The distal end of the stiffer sheath section 60 is affixed to the proximal end of the expandable sheath section 55 by any conventional means as adhesive 95 or heat bonding. Adhesives 95 may be made from Cyanoacrylates such as Loctite® manufactured by Loctite Corp. in Hartford Conn., or from ultraviolet light cured adhesives, or from polyurethane adhesives available from the H. B. Fuller Co. of St. Paul, Minn. A radio frequency bond could also be substituted for adhesive 95.

The balloon expandable stent 10 can be made of an inert, biocompatible material with high corrosion resistance that can be plastically deformed at low-moderate stress levels such as tantalum, the preferred embodiment. Other acceptable materials include stainless steel, titanium ASTM F63-83 Grade 1, niobium or high carat gold K 19-22. A self-expanding device can be made by the use of superelastic (nickel titanium) NiTi such as NiTi manufactured by Memory Corporation or Forukawa.

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10 | Stent |
| 15 | Guidewire Shaft |
| 20 | Guidewire Lumen |
| 25 | Inflation Shaft |
| 30 | Inflation Lumen |
| 35 | Balloon |
| 40 | Marker Band |
| 45 | Lesion |
| 50 | Vessel |
| 55 | Expandable Sheath Section |
| 60 | Stiffer Tubular Sheath Section |
| 65 | Distal End Cap |
| 70 | Proximal End Cap |
| 75 | Stent Delivery System |
| 80 | Adhesive |
| 85 | Proximal Cone |
| 90 | Distal Cone |
| 95 | Sheath Adhesive |

What is claimed is:

1. A method of delivering a stent into a body lumen comprising the steps of:

providing an inflation shaft defining an inflation lumen, the inflation shaft having a proximal end and a distal end;

providing an expandable balloon having a proximal end and a distal end, the balloon defining a balloon lumen, the proximal end of the balloon being sealingly affixed to the distal end of the inflation shaft;

providing a guidewire shaft defining a guidewire lumen, the guidewire shaft being coaxial with and running longitudinally through the inflation shaft lumen and through the balloon lumen, the guidewire shaft having a proximal end and a distal end;

providing a tubular sheath having a proximal end and a distal end, the tubular sheath defining a tubular sheath lumen, the inflation shaft extending longitudinally through the tubular sheath lumen;

providing an expandable sheath having a proximal end and a distal end, the proximal end of the expandable sheath being affixed to the distal end of the tubular sheath, the expandable sheath defining an expandable sheath lumen, the balloon extending longitudinally through the expandable sheath lumen;

providing an expandable stent with a radiopaque portion, the stent having a proximal end and a distal end, the stent being coaxially mounted upon the expandable sheath;

providing at least one radiopaque marker band affixed to the guidewire shaft proximal to the distal end of the balloon and distal to the proximal end of the balloon;

positioning the balloon within the expandable portion of the sheath such that the marker band is centered in the radiopaque portion of the stent in the body lumen at the treatment site; and inflating the balloon and the expandable sheath simultaneously to deploy the stent.

2. The method of claim 1 further comprising the steps of advancing the balloon out of the expandable sheath and into the treatment site and inflating the balloon.

3. The method of claim 2 further comprising the steps of deflating the balloon; and withdrawing the balloon into the expandable sheath.

4. The method of claim 1 further comprising the steps of advancing the balloon out of the expandable sheath and into the deployed stent and inflating the balloon.

5. The method of claim 4 further comprising the steps of deflating the balloon; and withdrawing the balloon into the expandable sheath.

6. The method of claim 1 further comprising the steps of:

releasing end caps securing the stent to the sheath.

7. The method of claim 6 wherein the step of releasing end caps comprises expanding the end caps.

* * * * *